United States Patent [19]

Marnett et al.

[11] Patent Number: 4,780,281

[45] Date of Patent: Oct. 25, 1988

[54] METHOD FOR ASSAY OF PEROXIDASE ENZYME OR REDUCING SUBSTRATE ACTIVITY

[75] Inventors: Lawrence J. Marnett, Pleasant Ridge; Paul E. Weller, Grosse Pointe Park, both of Mich.

[73] Assignee: Wayne State University, Detroit, Mich.

[21] Appl. No.: 744,673

[22] Filed: Jun. 14, 1985

[51] Int. Cl.$^4$ .............................................. C12Q 1/28
[52] U.S. Cl. .................................... 435/28; 435/803; 435/810
[58] Field of Search ....................... 435/28, 803, 810; 210/635, 656, 632

[56] References Cited

U.S. PATENT DOCUMENTS 4,302,537 11/1981 Gundermann et al. ............. 435/28
4,492,754 1/1985 Trager et al. ........................ 435/28

OTHER PUBLICATIONS

Samokyszyn et al., Oct. 30, 1984, Biochemical and Biophysical Research Communications, vol. 124, No. 2, pp. 430–436.
Snyder et al, (1979), Introduction to Modern Liquid Chromatography, John Wiley and Sons, Inc., N.Y., pp. 551–553.
Saunders, B. C., Helmes-Siedle, A. C. and Strok, B. P., (1964), in Peroxidase, Butterworth, Wash., (General Treatise and will be Supplied upon request).
Mair, R. D., Hall, R. T., (1971), in Treatise on Analytical Chemistry, Part II, vol. 14, (Kolthoff, I. M., Elvin, P. J., eds), pp. 295–434, (General Treatise and will be Supplied upon request).
Chance, B. and Maehley, A. C., (1964), in Methods in Enzymology, vol. 2, pp. 764–775.
Nagataki, S., Uchimura, H., Masuyama, Y., and Nakao, K., (1973), Endocrinology, 92, 363–371.
Nagasaka, A. and Hidaka, H., (1976), J. Clin. Endocrinol. Metab., 43, 152–158.
Hosoya, T., Kondo, Y. and Ui, N., (1962), J. Biochem., 52, Biochem., 52, 180–189.
Harauchi, T. and Yoshizaki, T., (1982), Anal. Biochem., 126, 276–284.
Maehly, A. C. and Chance, B., (1954), in Methods of Biochemical Analyses, (Glick, D. ed.), vol. I, pp. 357–424.
Nickel, K. S. and Cunningham, B. A., (1969), Anal. Biochem., 27, 292–299.
Puget, K., Michelson, A. M. and Arameus, S., (1977), Anal. Biochem., 79, 447–456).
Zaitsu, K. and Ohkura, Y., (1980), Anal. Biochem., 109, 109–113.
Makinen, K. K. and Tenovuo, J., (1982), Anal. Biochem., 126, 100–108.
Marklund, S. Ohlsson, P. I., Opara, A. and Paul, K. G., (1974), Biochim. Biophys. Acta, 350, 304–313.
Pace-Asciak, C. R., Smith, W. L., (1983), in The Enzymes, vol. 16, pp. 544–603.

(List continued on next page.)

*Primary Examiner*—Robert J. Warden
*Assistant Examiner*—William J. Herald
*Attorney, Agent, or Firm*—Ian C. McLeod

[57] ABSTRACT

A preferred method wherein 5-phenyl-4-pentenylhydroperoxide (PPHP) is reduced to 5-phenyl-4-pentenyl-alcohol (PPA) by plant and animal peroxidases in the presence of reducing substrates is described. The method also uses related homologs containing 3 to 8 carbon atoms. PHP and PPA are rapidly isolated with solid phase extraction, separated by isocrated reverse phase high performance liquid chromatography, and quantitated with a fixed-wavelength ultraviolet detector. The procedure described in suitable for detecting peroxide reducing enzymes, determining the kinetic properties of heme- and non-heme-containing peroxidases, and evaluating oxidizable compounds as reducing substrates for peroxidases. The method identifies compounds which are reducing substrates and also ranks them for relative activity. The method can be used to identify active antithrombotic, antimetastatic, or anti-inflammatory drugs as substrates as well as detect and characterize mammalian peroxidases.

18 Claims, 6 Drawing Sheets

U.S. PATENT DOCUMENTS

Aust, S. D. and Svingen, B. A., (1982), in Free Radicals in Biology, vol. V, pp. 1–28.

Warso, M. A. and Lands, W. E. M., (1984), Clin. Physiol. Biochem., 2, 70–77.

Lands, W. E. M., Kulmacz, R. J. and Marshall, P. J., (1984), in Free Radicals in Biology, vol. VI, pp. 39–62.

Paul, R., Riobe, O., Maumy, M., Zaiko, E. J. and House, H. O., (1975), Organic Synthesis, 55, 62–67.

Jackman, L. M. and Sternhell, S., (1969), Applications of Nuclear Magnetic Resonance Spectroscopy in Organic Chemistry. Sec. Ed., pp. 115–157.

Williams, H. R. and Mosher, H. S., (1954), J. Amer. Chem. Soc., 76, 2984–2990.

Wawzonek, S., Klimstra, P. D. and Kallio, R. E., (1960), J. Org. Chem., 25, 621–623.

Abraham, M. H., Davies, A. G., Liewellyn, D. R. and Thain, E. M., 1957, Anal. Chim. Acta, 17, 499, 503.

Porter, N. A., Funk, M. O., Gilmore, D., Isaac, R., Nixon, J., (1976), J. Amer. Chem. Soc., 98, 6000–6005.

Cleland, W. W., (1970), in The Enzymes, vol. 2, (Boyer, D. ed.), Academic Press, New York, pp. 1–79.

Chance, B. and Maehly, A. C., (1964), in Methods in Enzymology, (Colowick, S. D. and Kaplan, N. O. eds.), vol. 2, pp. 764–775.

Shannon, L. M., Kay, E., Lew, J. Y., (1966), J. Biol. Chem. 241, 2166–2172.

Critchlow, J. E. and Dunford, H. B., (1972), J. Biol. Chem., 247, 3703–3713.

McCarthy, M. B. and White, R. E., (1982), J. Biol. Chem., 258, 9153–9158.

Marnett, L. J., Siedlik, D. H., Ochs, R. C., Pagels, W. R., Das, M., Honn, K. V., Warnock, R. H., Tainer, B. E. and Eling, T. E., (1984), Molecular Pharm., 26, 328–335.

Marnett, L. J., (1984), in Free Radicals in Biology, vol. VI, pp. 63–94.

METHOD FOR ASSAY OF PEROXIDASE ENZYME OR REDUCING SUBSTRATE ACTIVITY

BACKGROUND OF THE INVENTION (1) Field of the Invention

The present invention relates to a method for assaying peroxidase enzyme activity and/or the ability of a compound (or mixture) to serve as a reducing substrate in a peroxidase catalyzed reaction (i.e. its suitability or activity for this purpose). In particular the present invention uses a hydroperoxyphenyl alkene as a reactant in the assay which is reduced to the corresponding hydroxide. This work was sponsored by the National Institute of Health (GM23642).

(2) Prior Art

Peroxidases reduce hydroperoxides to alcohols at the expense of electron donors. (FIG. 6). Theoretically, peroxidase activity can be assayed by measuring either the reduction of hydroperoxide or the oxidation of an electron donor (Saunders, B. C., Helmes-Siedle, A. C. and Stork, B. P. (1964) in Peroxidase, Butterworth, Washington). Residual hydroperoxide can be determined titrimetrically or spectrophotometrically but the procedures are time-consuming and of limited specificity (Saunders, B. C., Helmes-Siedle, A. C. and Stork, B. P. (1964) in Peroxidase, Butterworth, Washington; Putter, J. (1962) Hoppe Seylers Z. Physiol. Chem. 329, 40-51; Mair, R. D., Hall, R. T. (1971) in Treatise on Analytical Chemistry, Part II, Vol. 14-(Kolthoff, I. M., Elving, P. J. eds.) Wiley-Interscience New York, pp. 295-434). Production of alcohol has been quantitated for cumene hydroperoxide and fatty acid hydroperoxides but these compounds are not substrates for many heme-containing peroxidases. Fatty acid hydroperoxides undergo rearrangements to non-ultraviolet absorbing compounds in the presence of heme complexes. Therefore, assays based upon their formation are not general. Most quantitative assays for peroxidase activity are based on the conversion of an electron donor into a chromogenic, fluorometric, or chemiluminescent species. A broad range of electron donors are oxidized by heme-peroxidases (Chance, B. and Maehly, A. C. (1964) in Methods in Enzymology (Colowick, S. D. and Kaplan, N. O. eds) Vol. 2, p. 764-775, Academic Press, New York). Frequently used electron donors are guaiacol (Chance, B. and Maehly, A. C. (1964) in Methods in Enzymology (Colowick, S. D. and Kaplan, N. O eds) Vol. 2, p. 764-775, Academic Press, New York; Nagataki, S., Uchimura, H. Masuyama, Y. and Nakao, K. (1973) Endocrinology 92, 363-371; Nagusaka, A. and Hidaka, H. (1976) J. Clin. Endocrinol. Metab. 43, 152-158; Hosoya, T., Kondo, Y, and Ui, N. (1962) J. Biochem. 52, 180-189; Horuchi, T. and Yoshizaki, T. (1982) Anal. Biochem. 126, 276-284; Maehly, A. C. and Chance, B. (1954) in Methods of Biochemical Analyses (Glick, D. ed.) Vol. I, pp. 357-424, Interscience, New York), mesidine (Saunders), various leuko-dyes (Saunders; Nickel, K. S. and Cunningham, B. A. (1969) Anal. Biochem. 27, 292-299), luminol (Puget, K., Michelson, A. M. and Arameus, S. (1977) Anal. Biochem. 79, 447-456), phenols (Zaitsu, K. and Ohkura, Y. (1980) Anal. Biochem. 109, 109-113; Makinen, K. K. and Tenovuo, J. (1982) Anal. Biochem. 126, 100-108) and reduced cytochrome c (Saunders; Puffler). Many of these compounds produce multiple products (Saunders, Chance) or undergo reactions with time courses markedly delayed relative to peroxide reduction (Saunders). Therefore, the stoichiometry of peroxide reduction cannot always be determined. In addition, significant electron donor specificity exists between isoenzymes and different peroxidases (Marklund, S. Ohlsson, P. I., Opara, A. and Paul, K. G. (1974) Biochim. Biophys. Acta 350, 304-313), which limits the generality of a given assay.

Hydroperoxides are key intermediates of prostaglandin, thomboxane, leukotriene, and lipoxin biosynthesis as well as initial products of lipid peroxidation (Pace-Asciak, C. R., Smith, W. L. (1983) in The Enzymes Vol. 16 (Boyer, P.D. ed.) Academic Press New York, pp. 544-603; Aust, S. D. and Svingen, B. A. (1982) in Free Radicals in Biology, Vol. V. (Pryor, W. A. ed.) Academic Press Orlando, pp. 1-28). An increasing body of evidence suggests that they attain significant levels in tissues and body fluids and that they are important regulators of enzyme activity, inflammation, thombosis, and metastasis (Warso, M. A. and Lands, W. E. M. (1984) Clin. Physiol. Biochem. 2, 70; Lands, W. E. M., Kulmacz, R. J. and Marshall, P. J. (1984) in Free Radicals in Biology, Vol. VI (Pryor, W. A. ed.) Academic Press Orlando, pp. 39-62). This suggests the importance of identifying enzymes that reduce peroxides and quantifying their capacity for hydroperoxide reduction.

Objects

It is therefore an object to provide a method which quantitates a residual organic hydroperoxide and product alcohol simultaneously by employing high pressure liquid chromatography HPLC) with ultraviolet detection. Further it is an object to provide an assay for a peroxidase or reducing substrate which is rapid, sensitive, and specific. Further still it is an object to provide a method which is general for all peroxidases tested and which is amenable to automation. Further still it is an object of the present invention to provide assay for peroxidases based on their true function, i.e. reduction of hydroperoxides. These and other objects will become increasingly apparent by reference to the following description and the drawings.

IN THE DRAWINGS

GENERAL DESCRIPTION

Figure 1:
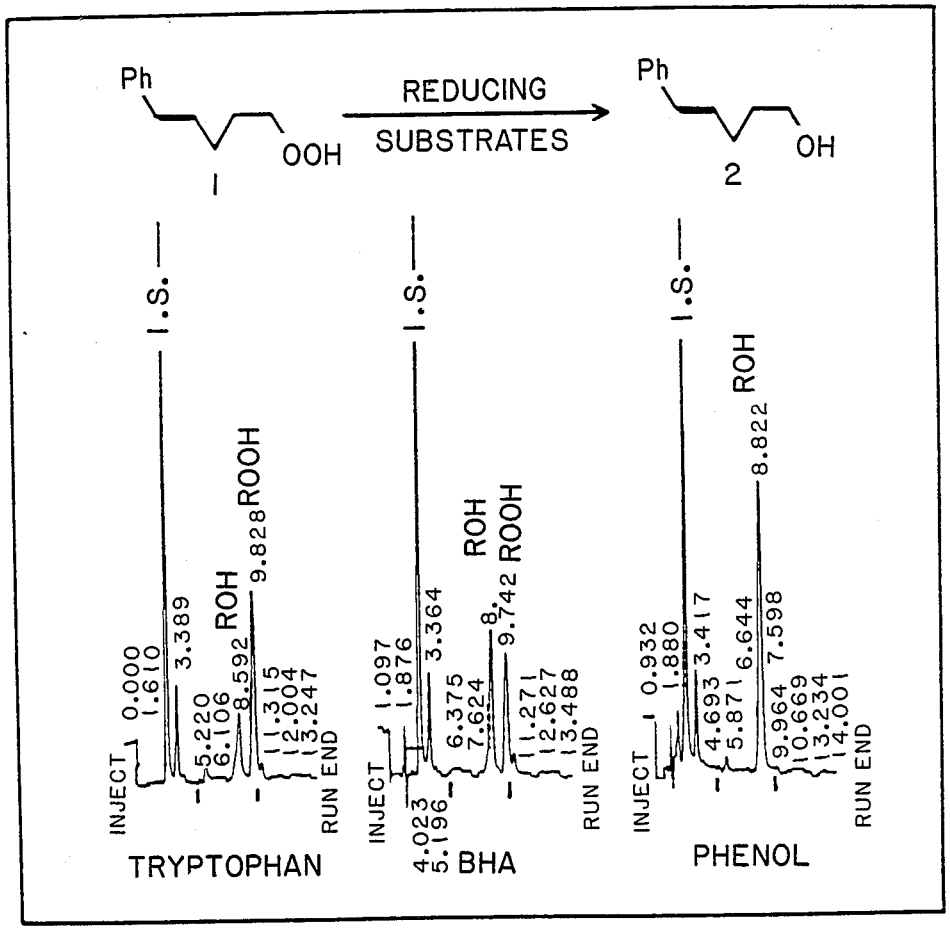
FIG. 1 is a chart showing high performance liquid chromatograms for incubations of 1-hydroperoxy-5-phenyl-4-pentene (PPHP) with three different reducing substrates and with horseradish peroxidase (HRP).

The present invention relates to a method for assay of peroxidase enzyme or reducing substrate activity which comprises:

reacting a mixture of 1-hydroperoxy-n-substituted and unsubstituted phenyl-(n-1)-alkene as a hydroperoxyalkene and a reducing substrate in the presence of a peroxidase enzyme in an appropriate solvent to produce 1-hydroxy-n-substituted and unsubstituted phenyl-(n-1)-alkene as a hydroxyalkene wherein the alkene group contains 3 to 8 carbon atoms and n is 5 to 8;

separating the hydroperoxyalkene and hydroxyalkene from the reacted mixture; and determining the concentration of the hydroperoxyalkene or hydroxyalkene based upon a liquid chromatographic separation.

The present invention particularly relates to a method for assay of peroxidase enzyme or reducing substrate activity which comprises:

reacting a mixture of 1-hydroperoxy-5-phenyl-4-pentene as a hydroperoxypentene and a reducing substrate in the presence of a peroxidase enzyme in an appropriate solvent to produce 1-hydroxy-5-phenyl-4-pentene as a hydroxypentene;

separating the hydroperoxypentene and hydroxypentene from the reacted mixture; and determining the concentration of the hydroperoxy pentene or hydroxypentene based upon a liquid chromatographic separation.

The present invention relates to a kit for assay of or reducing substrate activity which comprises:

1-hydroperoxy-n-substituted and unsubstituted phenyl-(n-1)-alkene as a hydroperoxyalkene;

a peroxidase enzyme; and a chromatographic column for separating the hydroperoxyalkene or a 1-hydroxy-n-substituted and unsubstituted phenyl-(n-1)alkene as a hydroxyalkene produced therefrom by the peroxidase enzyme.

SPECIFIC DESCRIPTION

The following chemicals were purchased as analytical grade reagents and used without purification: 1-ascorbic acid, butylated hydroxyanisole (BHA), butylated hydroxytoluene (BHT), 1-cysteine, diethyldithiocarbamic acid, d,1-epinephrine, guaiacol, reduced glutathione, indole-3-acetic acid, d,1-methionine, reduced nicotinamide adenine dinucleotide (NADH), reduced nicotinamide adenine dinucleotide phosphate (NADPH), polyoxyethylene sorbitan monolaurate (Tween-20), d,1-thiotic acid (lipoic acid), 1-tryptophan, and uric acid (Sigma Chemical Company); aniline, citric acid, sodium dibasic phosphate, sodium monobasic phosphate, potassium hydroxide, and pyridine (Spectrum Chemical Manufacturing Corporation); 30% hydrogen peroxide, hydroquinone, sodium chloride, anhydrous sodium sulfate, and potassium iodide (J. T. Baker Chemical Company); phenol and pyrogallol (Matheson, Coleman and Bell Manufacturing Chemists); and 1,3-diphenylisobenzofuran (DPBF) (Aldrich Chemical Company).

Synthesis of 5-Phenyl-4-pentenyl-alcohol (PPA)

PPA was prepared by the method of Paul et al. (Paul, R., Riobe, O., Maumy, M., Zaiko, E. J. and House, H. O. (1975) Organic Synthesis 55, 62–67; Paul, R. (1944) C.R.H. Acad. Sci. 218, 122). The alcohol was purified by medium pressure liquid chromatography (MPLC) on silica. Overall yield after purification was 60%. The alcohol was a clear colorless liquid, B.P. (1 mm Hg, vacuum vigreux) 108°–112° C., and had an ultraviolet maximum at 257 nm ($\epsilon = 11,400$). A complete proton NMR has not been previously reported (Jackman, L. M. and Sternhell, S. (1969) Applications of Nuclear Magnetic Resonance Spectroscopy in Organic Chemistry. Second Ed. Pergamon Press (New York), p. 115–157). The proton NMR (300 MHz, CDCl$_3$, relative to TMS internal) was $H_1$, 3.75 ppm, t, 2H; $H_2$, 1.75 ppm, m (t,t), 2H; $H_3$, 2.30 ppm q (d,t) 2H; $H_4$, 6.20 ppm, m (d,t), 1H, $J_{H3-H4}=6.18$ Hz; $H_5$, 6.40 ppm, d, $J_{H4-H5}=15.8$ Hz; Ph-H, 7.30 ppm, m, 5H; R-OH, ~1.4 ppm, broad s, ~1H. The chemical shifts, coupling pattern, and coupling constants indicate a trans-benzylic olefin (Jackman, L. M. and Sternhell, S. (1969) Applications of Nuclear Magnetic Resonance Spectroscopy in Organic Chemistry. Second Ed. Pergamon Press (New York), pp. 115–157; Bakassian, G., Descotes, G., and Sinou, D. (1970) Bull. Soc. Chem. Fr. 7084–7089).

Synthesis of 1-hydroperoxy-5-Phenyl-4-pentene (PPHP)

The method of Williams and Mosher (Williams, H. R. and Mosher, H. S. (1954) J. Amer. Chem. Soc. 76, 2984–2990) with modifications similar to Wawzonek et al. (Wawzonek, S., Klimstra, P. D. and Kallio, R. E. (1960) J. Org. Chem. 25, 621–623) (equation 1) gave PPHP. The same procedure can be used for other hydroperoxyalkenes.

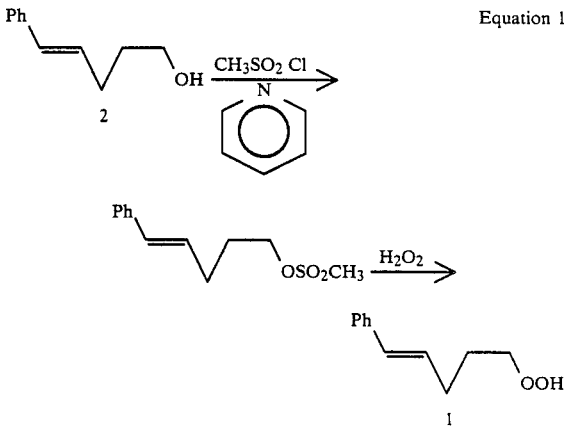

Equation 1

PPA was converted to a poorly soluble mesylate by this procedure. Displacement of the mesylate by alkaline hydrogen peroxide required solubilization of the mesylate in an unusually large volume of methanol. The only water introduced into the reaction mixture was present in the 30% hydrogen peroxide used. A typical preparation follows:

Dry pyridine (18.5 mmol) was slowly added (60 min) to a stirred mixture of methanesulfonyl chloride (11.1 mmol) and PPA (9.3 mmol) maintained at 10° C. The reaction was stirred an additional 30 minutes and then poured into 100 ml of ice-cold 10% v/v concentrated hydrochloric acid. This solution was extracted with two 75 ml portions of diethyl ether and the ether layers combined and washed with 50 ml of water, and then 50 ml of ice-cold 5% w/v aqueous sodium bicarbonate solution. The ether was removed by rotary-evaporation. This residue was used without purification for the hydroperoxide preparation.

The mesylate was dissolved in 700 ml of methanol and cooled to 0° C. with stirring. Thirty percent hydrogen peroxide (1.02 mol) and powdered potassium hydroxide (0.417 mol) were added and the mixture stirred at 10° C. After 30 min, the mixture was allowed to warm to room temperature and stirred for 15 hours. The hydroperoxide was isolated by diluting the mixture with 100 ml of saturated aqueous sodium chloride, cooling to 1° C., and adjusting the pH to approximately 7 with concentrated hydrochloric acid. The pH 7 mixture was extracted with three 100 ml aliquots of benzene. The benzene extracts were combined, washed with 50 ml of water, dried with anhydrous sodium sulfate, filtered, and concentrated to a residue by rotary-evaporation. The residue was dissolved in 5% v/v ethyl acetate-hexane and the hydroperoxide purified by MPLC on silica with elution by stepwise sequential increase of mobiles from hexane to 25% v/v ethyl acetate-hexane in 5% increments. PPHP was isolated in 72% yield from PPA. It was stored as a dry residue under argon at $-80°$ C.

PPHP is a very slightly yellow liquid with a characteristic peroxide odor. It gives a positive peroxide test with ferrous thiocyanate spray on TLC (Abraham, M. H., Davies, A. G., Liewellyn, D. R. and Thain, E. M. (1957) Anal. Chim. Acta 17, 499,503). The ultraviolet spectrum exhibits a maximum at 257 nm ($\epsilon = 11,400$). The proton NMR (300 MHz, CDCl$_3$, relative to TMS internal) was H$_1$, 4.05 ppm, t, 2H; H$_2$, 1.75 ppm, m (t,t), 2H; H$_3$, 2.30 ppm, q(d,t), 2H; H$_4$, 6.20 ppm, m (d,t), $J_{H3-H4} = 6.92$ Hz; H$_5$, 6.40 ppm, d, $J_{H4-H5} = 15.8$ Hz; Ph-H, 7.30 ppm, m, 5H; ROOH, 8.41 ppm, s, 1H. The spectrum was consistent with a trans-benzylic olefin (Jackman, L. M. and Sternhell, S. (1969) Applications of Nuclear Magnetic Resonance Spectroscopy in Organic Chemistry. Second Ed. Pergamon Press (New York), pp. 115–157) and a primary hydroperoxide (Porter, N. A., Funk, M. O., Gilmore, D., Isaac, R., Nixon, J. (1976) J. Amer. Chem. Soc. 98, 6000–6005).

Enzyme Preparation

Horseradish peroxidase (HRP) was desalted on an exclusion column to eliminate small molecules that could have potentially acted as electron donors. HRP (Sigma Chemical Corporation, Type VI) was dissolved in a minimum of 0.1 M potassium citrate buffer, pH 5.5 and desalted on a Sephadex G-15 column (1×10 cm, Pharmacia Fine Chemicals) with elution by the same buffer. Fractions absorbing at 280 nm were pooled and diluted with 0.1 M potassium citrate buffer, pH 5.5 as required to make a 71.9 microM stock for storage. This solution was protected from light and stored at 5° C. A 328 nM working solution for steady-state assays was prepared daily by diluting the 71.9 microM HRP stock with 0.1 M potassium citrate, pH 5.5. A 5.0 microM working solution for reducing substrate specificity assays was prepared daily by diluting the 71.9 microM HRP solution with 0.1 M potassium citrate buffer, pH 5.5.

Incubations, Sample Preparation, and Analysis

Incubations were performed in triplicate with a 25° C. shaker bath in 16×150 mm disposable glass test tubes. 60 nM HRP was incubated at 25° C. in 0.1 M potassium citrate buffer, pH 5.0 containing 0.2 mM Tween 20, with 100 microM PPHP and 200 microM potential reducing substrate. The index value is defined as, Index=concentration PPA/(concentration PPA + concentration PPHP). Most reducing substrates were prepared daily as 8 mM stocks in either water, methanol, or methanol:water (1:1 v/v). DPBF was dissolved in acetone. Uric acid was dissolved in DMSO. Epinephrine required titration with dilute hydrochloric acid prior to dissolution in methanol. Indoleacetic acid, tryptophan, cysteine, and methionine were titrated with dilute potassium hydroxide prior to dissolution in methanol:water (1:1 v/v).

For the data in Table 1 hereinafter, reducing substrates (50 microliters of 8 mM stocks—see Table 1 for preparation) were transferred into 1.9 ml of 0.1 M potassium citrate buffer, pH 5.5, containing 0.2 mM Tween-20 and allowed to thermally equilibrate for 10 minutes. HRP (24 microl of a 5 microM stock) was added to each trial and preincubated for three minutes prior to the addition of PPHP (25 microl of 8 mM stock in methanol). Incubations were stopped at 6 minutes by pouring mixtures onto Baker SPE System columns (3 ml octyldecylsilyl, from J. T. Baker & Co.). The columns were prepared prior to use by passing 3×3 ml aliquots of water through the columns with the Baker SPE vacuum system. At the stop time, an individual trial was poured onto the column and aspirated to near dryness. Each individual trial was set aside until the reminder of the trials were treated in the same manner. After all incubation trials were partitioned onto the SPE columns, each individual incubation tube was washed with 2 ml of 0.2 mM Tween 20 in distilled water and poured onto the corresponding SPE column. This Tween 20/water wash was aspirated to near dryness with vacuum. Analytes were eluted into 12×76 mm disposable glass test tubes with 2×1 ml aliquots of methanol (HPLC grade, Fisher Scientific Co.). The sample collection rack for the Baker 10 SPE System was modified to accommodate these 12 mm diameter tubes. The SPE columns were aspirated dry at this point and discarded. An internal chromatographic standard of p-nitrobenzyl alcohol (25 microl of 8 mM stock solution in methanol) was added to each methanol eluent, mixed by vortexing, and then clarified by filtration through a 0.45 micron nylon Swinney type filter (Rainin Instrument Corp.). The filtered eluents were used directly for chromatographic analysis.

Chromatographic conditions were as described hereinafter and the results are shown in part in FIG. 1.

The Initial incubation conditions were 0.1 M potassium citrate buffer, pH 5.5, with 0.2 mM Tween 20, 200 microM reducing substrate, 60 nM HRP and 10 microM PPHP (structure 1). HRP-catalyzed reductions of PPHP to PPA (structure 2) for good (phenol), moderate (BHA), and poor (tryptophan) reducing substrates are illustrated for the reducing substrate specificity assay. Typical analyte resolutions are also shown.

Quantitation was determined by adding an internal standard (p-nitrobenzyl alcohol: annotated as I.S. on chromatograms) and ratioing peak areas. Chromatograms are 40 microliters injections onto a 5 micron Zorbax octylsilyl reverse-phase column (DuPont Instrument Corp.) with an isocratic elution mobile of 56% v/v methanol in water at 2 ml per min. U.V. monitoring was with a fixed 254 nm detector (Varian 5000, Varian Instrument Corp.). Vertical numbers are associated with peak retention times in minutes (the integrator used was a Vista 402 System, Varian Instruments).

Analyte concentrations were calculated by an internal standard method of calculation. This required individual incubation chromatograms to be compared to a calibration chromatogram generated by chromatographing a 40 microliter sample aliquot of a solution of PPHP as described under calculations.

Figure 3:
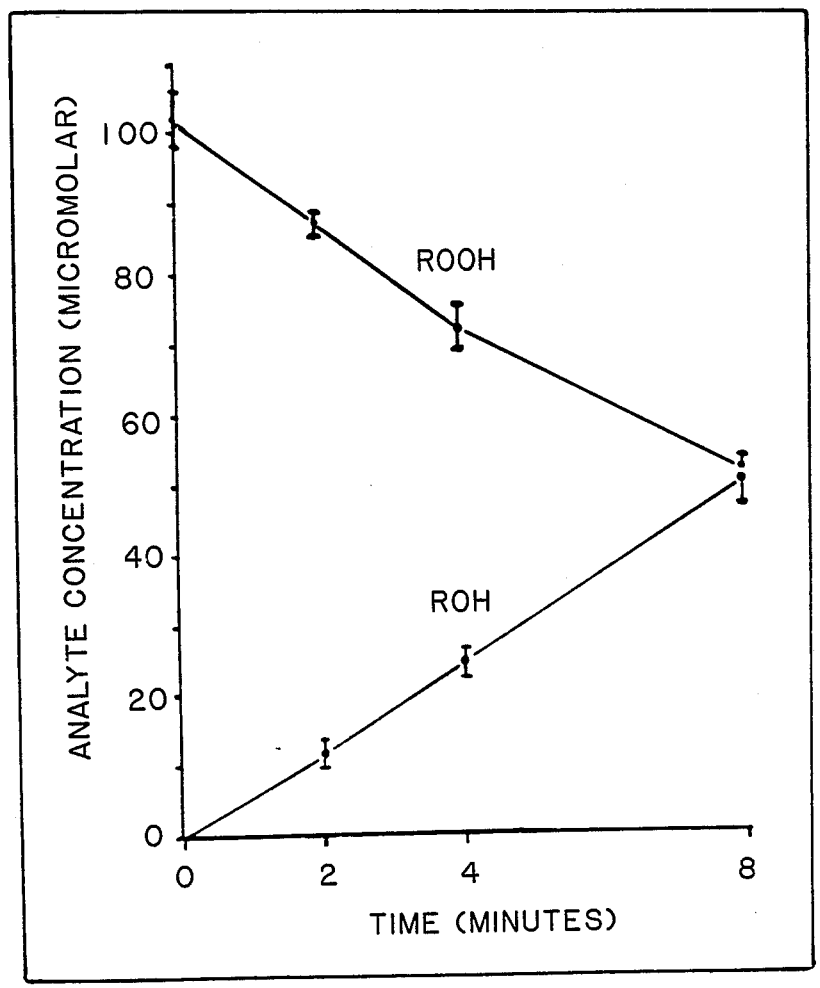
FIG. 3 shows the time course for HRP reduction of PPHP.
Figure 4A:
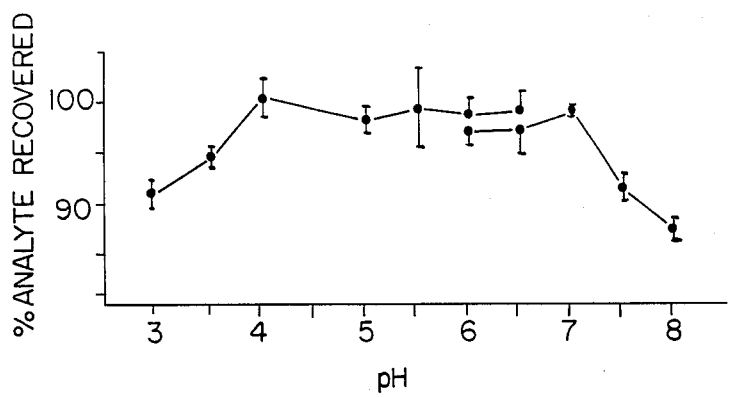
FIGS. 4 and 4a show analyte recovery and pH optimum for production of 1-hydroxy-5-phenyl-4-pentene (PPA) by HRP and the reducing substrate phenol.
Figure 4:
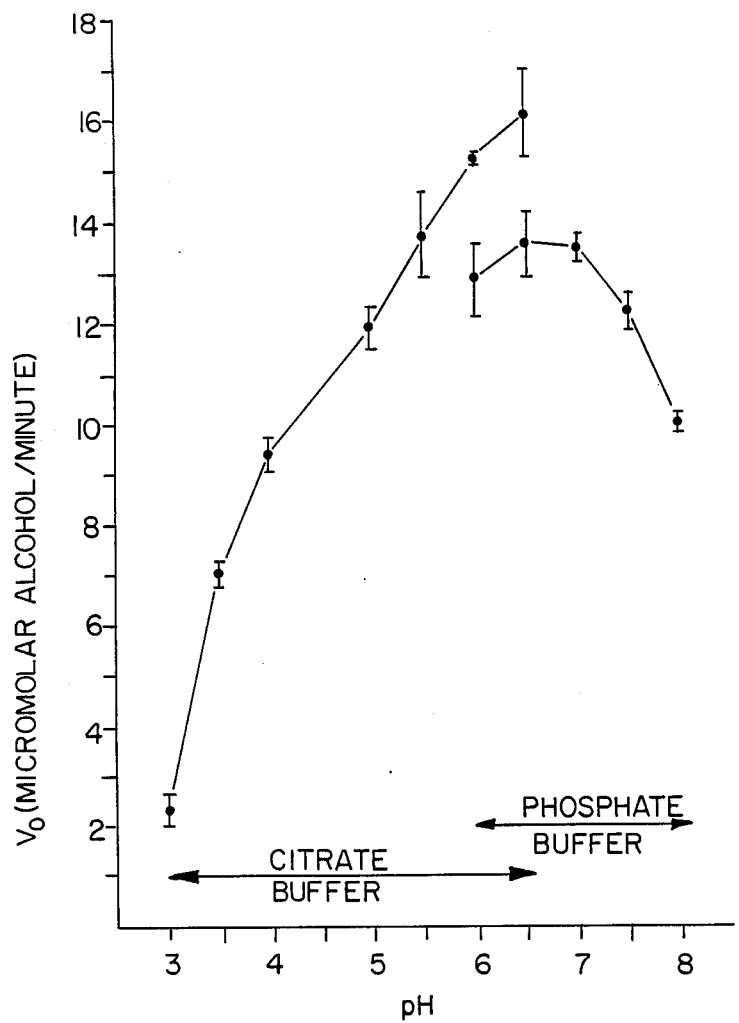
Figure 5:
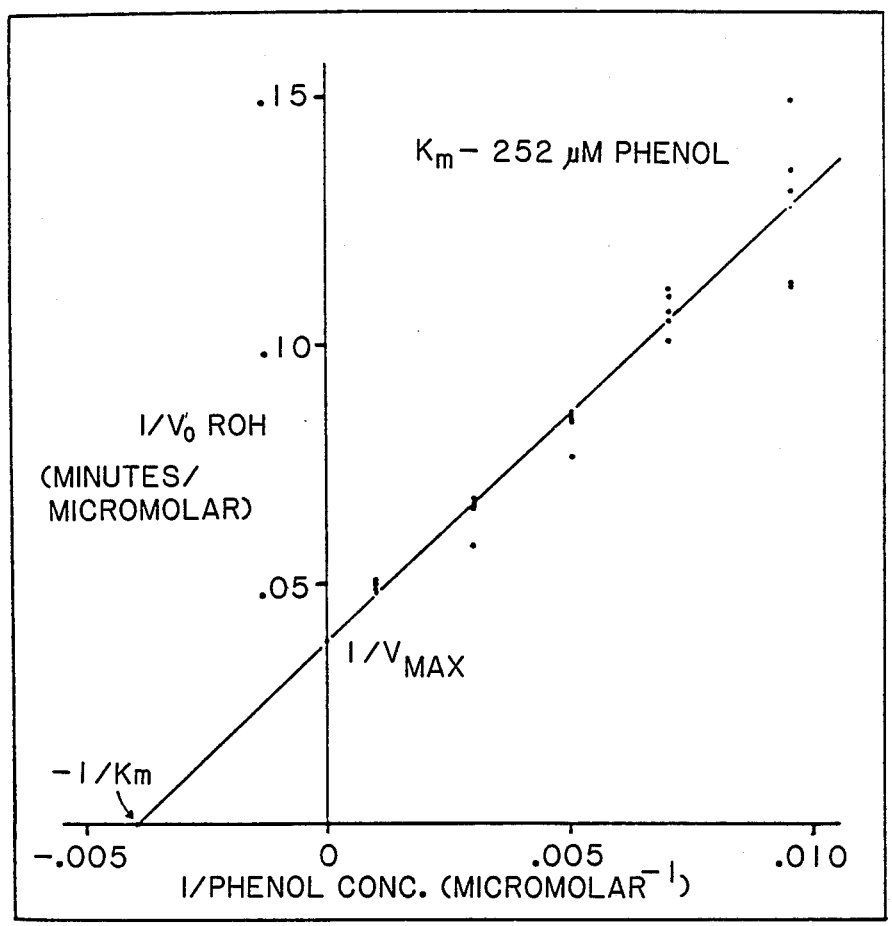
FIG. 5 is a double reciprocal plot of initial velocities of (PPA) versus phenol concentration.

Steady-state kinetic assay specifics are shown in FIGS. 3, 4 and 5 and were as follows: FIG. 3 shows the time course for HRP reduction of PPHP. Incubations were performed with 2.5 nM HRP and 200 microM phenol as reducing substrate in 0.1 M citrate and 0.2 mM Tween 20 buffer at pH 5.5 with 100 microM hydroperoxide. The incubations were terminated at 2, 4, and 8 minutes by pouring the incubations onto SPE columns as described in Methods. All of the other conditions were as described for FIG. 1. The data points are the average of triplicates. FIG. 4 shows analyte recovery and FIG. 4a shows pH optimum for the production of PPA by HRP and Phenol. pH Optimum. (FIG. 4) HRP (2.5 nM) was incubated in either 0.1 M potassium citrate buffer or in 0.1 M sodium-hydrogen-phosphate buffer with 100 microM PPHP and 200 microM phenol. All buffers contained 0.2 mM Tween-20. Incubations were stopped at 4 minutes by pouring onto SPE columns as described in Methods. Each data point is the average of triplicates. Total Recovery of PPA and PPHP. (FIG. 4a) Total Recovery of analytes over the same pH range as the pH optimum experiment was determined by the following formula.

$$\% \text{ Recovery} = \frac{\text{Concentration of } PPA + \text{Conc. } PPHP}{100 \text{ microM initial } PPHP} * 100$$

FIG. 5 shows a double reciprocal plot of initial velocities of PA production versus phenol concentration. HRP (2.5 nM) was incubated in 0.1 M potassium citrate buffer, pH 5.5 containing 0.2 mM Tween-20, with 100 microM PPHP and phenol concentrations of either 1 mM, 300microM, 200 microM, 142 microM, or 105 microM. Incubations were stopped at 4 minutes by pouring on SPE columns as described in Methods. PPA concentrations were converted into velocities by dividing by the incubation time and assuming linear steady-state velocities over the first 8 minutes (see FIG. 3). Five replicates of each phenol concentration were assayed. $K_m$ and $V_{max}$ were determined by linear regression analysis upon the non-averaged data points.

Calculations

The following general formula was used to calculate the concentrations of PPA and PPHP from incubation trials.

Conc. Analyte (microM) =

$$\frac{R \text{ (incubation chromatograms)}}{R \text{(calibration chromatogram)}} * 100 \text{ uM}$$

where: R (incubation chromatogram) is the response ratio for either analyte in the incubation chromatogram defined as peak area of either PPA or PPHP/peak area of internal standard, and R (calibration chromatogram) is the response ratio for PPHP in the calibration chromatogram defined or peak area of PPHP/peak area of internal standard. Identical response ratios for PPA and PPHP relative to the internal standard allowed the use of a calibration chromatogram of one analyte, that is, PPHP, prepared by adding 25 microl of 8 mM PPHP and 25 microl of 8 mM p-nitrobenzyl alcohol to 2 ml of 56% v/v methanol in water. (HPLC grade solvents. Fisher Scientific Co.).

Results

Figure 2:
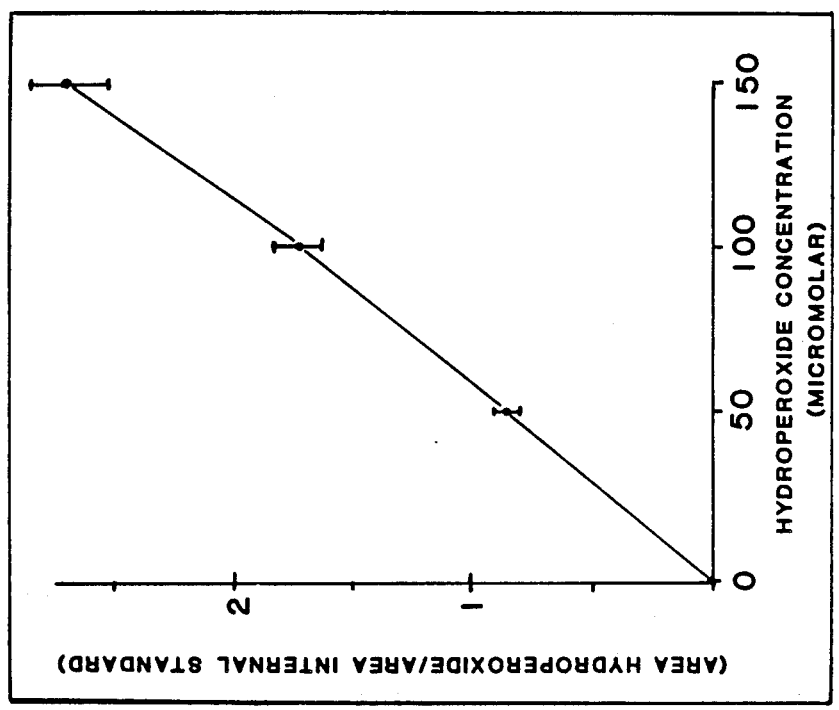
FIG. 2 shows the linearity of response of PPHP with concentration.

Typical chromatograms illustrating the separation of PPHP and PPA are presented in FIG. 1. PPA and PHP were resolved with baseline separation. Variation in retention times for PHP and PPA were ±0.9% relative standard deviation (RSD) (N=25) and ±0.5% RSD (n-28) respectively. Replicate response ratio variation for 100 microM PPHP solutions carried through the chromatographic analysis was 2.5% RSD (n-10). Identical 100 microM PPHP solutions in 0.1 M potassium citrate buffer pH 5.5 containing 0.2 mM Tween-20 carried through the SPE workup and chromatographic analysis demonstrated replicate response ratio variation of 3.4% RSD (n-10). Total recovery exceeded 95% in all cases. FIG. 2 illustrates a linear response ratio (defined as peak area of PPHP/peak area of internal standard) vs. PPHP concentration between 0 and 150 microM PPHP with 100 microM p-nitrobenzyl alcohol as internal standard. This linear response ratio was required for an internal standard method of calculation.

Verification of Metabolite Identity

The product from the incubation of HRP (60 nM) with 200 microM phenol and 100 microM PPHP was isolated by extraction and HPLC for comparison to synthetic PPA by NMR. These incubations involved a 10-fold scale-up relative to the procedure for reducing substrate specificity. The metabolite NMR was identical to that for synthetically prepared PPA.

Reducing Substrate Specificity Assay

Figure 6:
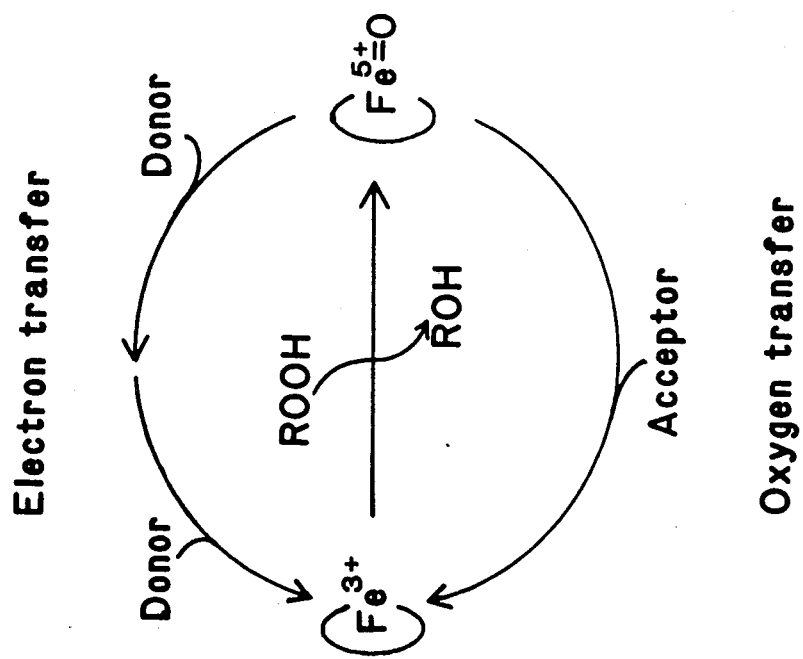
FIGS. 6 and 7 show the cycle in the determination of the peroxidases or reducing substrates.

A heme-peroxidase undergoes conversion to oxidized enzyme intermediates with the reduction of hydroperoxides. The oxidized enzyme cannot reduce additional hydroperoxide and requires reduction by two electrons to the resting enzyme. Thus hydroperoxide reduction cannot occur in the absence of a suitable electron donor (FIG. 6). The electron donor is properly called the reducing substrate, but has also been called the hydrogen donor or oxygen acceptor.

A comparison of the ability of 22 compounds to serve as reducing substrates for HRP is presented in Table 1.

TABLE 1.

| Reducing Substrate Specificity for HRP. | |
|---|---|
| Substrate | Index |
| 1. Aniline | 0.97 ± 0.01 |
| 2. Guaniacol | 0.97 ± 0.01 |
| 3. Hydroquinone | 0.97 ± 0.01 |
| 4. Iodide | 0.97 ± 0.02 |
| 5. Phenol | 0.97 ± 0.01 |
| 6. Pyrogallol | 0.97 ± 0.01 |
| 7. Uric Acid | 0.96 ± 0.00 |
| 8. Diethyldithiocarbamate | 0.72 ± 0.02 |
| 9. BHA | 0.56 ± 0.01 |
| 10. Ascorbic Acid | 0.50 ± 0.00 |
| 11. Epinephrin | 0.39 ± 0.01 |
| 12. BHT | 0.19 ± 0.03 |
| 13. Indoleacetic Acid | 0.14 ± 0.01 |
| 14. Tryptophan | 0.13 ± 0.04 |
| 15. Glutathione | 0.07 ± 0.01 |
| 16. Cysteine | 0.06 ± 0.01 |
| 17. DPBF | 0.06 ± 0.01 |
| 18. NADPH | 0.06 ± 0.01 |
| 19. Lipoic Acid | 0.06 ± 0.01 |
| 20. Methionine | 0.05 ± 0.01 |
| 21. NADH | 0.05 ± 0.00 |
| 22. No Reducing Substrate | 0.04 ± 0.01 |

Compounds with high index values are good reducing ubstrates. FIG. 1 illustrates chromatograms for good, moderate and poor reducing substrates for HRP. A control in which reducing substrate was omitted produced a low index value that probably reflects the use of protein or other reactive components of the protein preparation as reducing substrates.

PPHP reduction with 60 nM HRP and 200 microM phenol is complete within one minute at 25° C. (data not shown). Therefore, kinetic differences due to reducing substrates are minimized and the index represents only whether a compound is a suitable reducing substrate. The 2 to 1 stoichiometry of reducing substrate to hydroperoxide was chosen to reflect the redox equivalents required for complete PPHP reduction. HRP concentrations of 15 and 30 nM (data not shown) gave similar index values to those tested in table 1 over six minute incubations.

Steady-State Kinetic Assays

The steady-state kinetic assays required a method for the rapid quantitative isolation of analytes from incubation mixtures. Preliminary experiments indicated that extraction with organic solvents was not suitable for times terminations. Solid phase extraction with disposable octadecylsilyl columns proved successful. A linear time course for the reduction of PPHP with HRP and phenol was demonstrated over 8 minutes (FIG. 3). We designed the assays with 4 minute termination times converting either the concentration of PPHP or PPA into velocities. The data in FIG. 3 indicate the validity of this step.

Saturation Parameters

Apparent $K_m$ values for reducing substrates and enzymatic turnover numbers are readily determined by the steady-state kinetic assay. FIG. 5 illustrates data as a double reciprocal plot of initial velocity of alcohol production versus phenol concentration. The approach to determining the $K_m$ for phenol was essentially as described by Cleland (Cleland, W. W. (1970) in The Enzymes, Vol. 2, (Boyer, D. ed.) Academic Press, New York, p. I-79). The apparent $K_m$ for phenol was 252 microM with an HRP turnover number (with phenol) of 10,500 min$^{-1}$ based upon a calculation from the $V_{max}$. The $K_m$ for PPHP was not readily determinable by this procedure because the detection of PPHP and PPA becomes more difficult at lower concentrations. We estimated the $K_m$ for PPHP with HRP to be 18 microM by using the spectrophtometric assay of Chance & Maehly (Chance, B. and Maehly, A. C. (1964) in Methods in Enzymology (Colowick, S. D. and Kaplan, N. O. eds.) Vol. 2, p. 764–775, Academic Press, New York) for quaiacol oxidation.

pH Optimum

A pH optimum for HRP based on initial linear velocities over 4 minutes with phenol as reducing substrate was determined. FIG. 4 illustrates an optimal velocity range for alcohol production between pH 6.5 and 7.0. The same velocity optimum exists for PHP reduction (data not shown). This optimum is related to the isoenzyme of HRP used and is consistent with the suppliers specifications for the enzyme, which states the presence of two basic isoenzymes (Shannon, L. M., Kay, E., Lew, J. Y. (1966) J. Biol. Chem. 241, 2166–2172). In conjunction with the pH optimum determination, analyte recovery over the same pH range was determined. The total percentage of PPHP and PPA recovered are illustrated in the top box of FIG. 4a. The reduced recovery below pH 3 and above pH 8 is related to metabolism of PPHP to undetermined products. Both PPHP and PPA are quantitatively recoverable from buffer without enzyme at these pH's.

Table 2 shows the efficiency of various reducing substrates for prostaglandin H synthase under the conditions for Table 1.

TABLE 2.

Index of Efficiency of Reducing Substrates for Prostaglandin H Synthase.

| COMPOUND | INDEX |
| --- | --- |
| 1. Sulindac Sulfide (Merck) | .96 |
| 2. BW-755-C (Bayer) | .96 |
| 3. Epinephrine | .92 |
| 4. Nafazatrom | .80 |
| 5. MK-447 (Merck) | .72 |
| 6. Oxyphenylbutazone (Ciba-Geigy) | .71 |
| 7. Flufenamate (Warner-Lambert) | .68 |
| 8. Phenol | .51 |
| 9. Methylphenyl Sulfide | .50 |
| 10. Diclofenac (Ciba-Geigy) | .50 |
| 12. Meclofenamate (Warner-Lambert) | .35 |
| 12. 5-Hydroxy-indomethacin (Merck) | .34 |
| 13. Piroxicam (Pfizer) | .34 |
| 14. MK-410 (Merck) | .26 |
| 15. Isoxicam (Pfizer) | .25 |
| 16. Monophenylbutazone (Ciba-Geigy) | .23 |
| 17. Phenylbutazone (Ciba-Geigy) | .23 |
| 18. No Reducing Substrate | .13 |
| 19. Ibuprofen (Upjohn) | .12 |
| 20. Flurbiprofen (Upjohn) | .12 |
| 21. Salicylic Acid | .06 |
| 22. Aspirin | .04 |

The results are similar to those shown in Table 1.

Discussion

A practical method is described for the determination of peroxidase enzyme activity that monitors the ability of enzyme preparations to reduce PPHP in the presence of a reducing substrate. PPHP is readily prepared from PPA and is stable if protected from light and metals. It is soluble in aqueous buffers but partitions into organic solvents or adheres to the stationary phases of an octyldecylsilyl solid phase extractor. The alcohol product and hydroperoxide substrate are conveniently separated by HPLC and reliably quantitated by ultraviolet detection. These properties make PPHP an ideal substrate for the assay. Of equal importance is the finding that PPHP is an excellent substrate for HRP, catalase, lactoperoxidase, protaglandin H (PGH) synthase, cytochrome P-450, and glutathione peroxidase. Thus, the procedure is a general assay for peroxidase activity.

A key feature of the method is the use of reverse phase SPE columns to extract PPA and PPHP from aqueous buffers. This enables reactions to be terminated and hydroperoxide removed from the enzyme rapidly (within 1–2s). This makes it possible to determine accurate rates of either hydroperoxide reduction or alcohol production and thereby calculate steady-state kinetic properties. Limiting concentrations of HRP (2.5 nM) reduced PPHP (100 microM) with a linear time course in the presence of 200 microM phenol (FIG. 3). Varying the phenol concentration indicated that the $K_m$ of HRP for phenol is 252 microM. In addition, it indicates the turnover number of PHP reduction is $10.5 \times 10^3$ min. Comparable literature data for phenol are not available, but the $K_m$ for the reaction of p-cresol with HRP compound II at pH 8.11 is apprximately 180 microM (Critchlow, J. E. and Dunford, H. B. (1972) J. Biol. Chem. 247, 3703–3713). The turnover for pyrogallol oxidation by a similar preparation of HRP isoenzymes as that used by us and, phenylperoxyacetic acid has recently been reported to be $1.85 \times 10^4$ min$^{-1}$ (McCarthy, M. B. and White, R. E. (1982) J. Biol. Chem. 258, 9153–9158). It is not possible to estimate how this number relates to the $V_{max}$ for reduction of phenylperoxyacetic acid. Nevertheless, the turnover numbers calculated for HRP action on the two organic peroxides by two different methods are of similar magnitude.

The fact that PPHP is a good substrate for a number of heme- and non-heme-containing peroxidases is unexpected and appears to be due to the fact that it contains a primary hydroperoxide. Similar results can be achieved with homologous compounds containing 3 to 8 carbon atoms. HRP, for example, utilizes primary hydroperoxides quite efficiently but not secondary or tertiary hydroperoxides.

Catalytic reduction of hydroperoxides by peroxidases does not occur in the absence of a reducing substrate (FIG. 6). Therefore, our assay procedure can be used to determine whether a given compound is a reducing substrate for the peroxidase under study. If high concentrations of enzyme and saturating concentrations of reducing substrates are used then hydroperoxide reduction is rapid and complete. If however, limiting concentrations of enzyme or less-than-saturating concentrations of reducing substrate are employed, the extent of reduction after a given time is related to the efficacy of a compound as a reducing substrate. We have compared the ability of a series of 21 compounds at concentrations of 200 microM to reduce 100 microM PPHP when incubated with 60 nM HRP. The stoichiometry of reducing substrate: hydroperoxide of 2:1 was chosen to maximize the possibility of one electron reduction of HRP compounds I and II generated during hydroperoxide metabolism. The results presented in Table 1 indicate that it is possible to use the assay to rank individual compounds with respect to their ability to support reduction. Excellent reducing substrates have high index values whereas compounds that are poor reducing substrates have very low index values. Such comparisons are useful in screening compounds that are efficient antagonists of peroxide-induced pathology by virtue of their ability to lower steady-state levels of peroxide. This reducing substrate activity has recently been proposed to explain the antithrombotic and antimetastatic effects of nafazatrom, for example (Marnett, L. J., Siedlik, D. H., Ochs, R. C., Pagels, W. R., Das, M., Honn, K. V., Warnock, R. H., Tainer, B. E. and Eling, T. E. (1984) Molecular Pharm. 26, 328–335).

Figure 7:
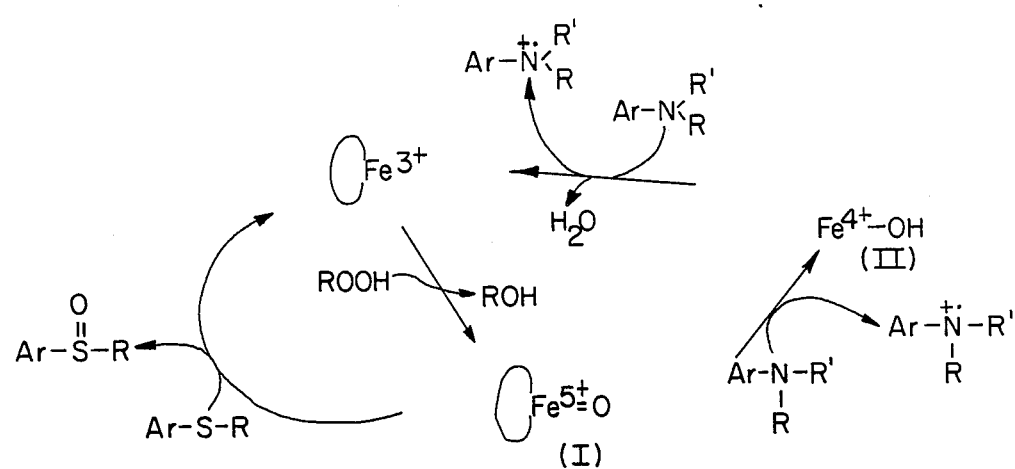

A corollary of the fact that a compound is a reducing substrate for a peroxidase is that it is oxidized by a higher oxidation state of the peroxidase. In the case of HRP, this corresponds to compound I or compound II as shown in FIG. 7. If a compound is oxidized in a hydroperoxide-dependent reaction but is not a reducing substrate for the peroxidases present in tissue, the oxidizing agent cannot be peroxidase higher oxidation states or catalytic hydroperoxide reduction would occur. For example, benzo[a]yrene, 7,8-dihydroxy-7,8-dihydrobenzo[a]pyrene, and diphenylisobenzofuran are oxidized by hydroperoxy intermediates of prostaglandin biosynthesis (Marnett, L. J. (1984) in Free Radicals in Biology, Vol. VI (Pryor, W. A. ed.) Academic Press, Orlando, pp. 63–94) but are not reducing substrates for PPHP reduction by prostaglandin H synthase. This implies that the oxidizing agents in each case are different than the peroxidase iron-oxo complexes. In fact, the results of detailed studies suggest that the oxidizing agents are peroxyl free radicals. Consequently the hydroperoxide-reduction assay provides information about the identity of oxidizing agents generated in hydroperoxide-dependent reactions.

All common prior art assays for peroxidase activity are based on the oxidation of the reducing substrate. The methods employed are usually spectrophotometric which makes them rapid and amenable to automation. However, the relationship of substrate oxidation to hydroperoxide reduction is not always clearcut because of the complexity of substrate oxidation process. In addition, the reaction of compounds that do not undergo spectral changes during oxidation cannot be followed directly. The method of the present invention requires only an isocratic high pressure liquid chromatography (HPLC) unit equipped with a 254 nm ultraviolet detector, a common piece of laboratory equipment that is less expensive than most spectrophotometers. We used an HPLC equipped with an autoinjector and data system to automate the chromatographic step of the assay. Using this system, we can perform 60 assays within a 24 hour period. However, the major advantage of the assay is not instrumental but is based on the fact that it directly quantitates the hydroperoxide-reducing capability of any substrate and peroxidase combination. This feature opens up exciting new possibilities for detecting and identifying peroxidases and peroxidase reducing substrates as well as accurately determining the kinetics of peroxide reduction.

We claim:

1. A method for assay of peroxidase or the ability of a compound to serve as a reducing substrate in a peroxidase catalized reaction which comprises:
   (a) reacting an effective amount of a mixture of 1-hydroperoxy-n-phenyl-(n-1)-alkene as a hydroperoxyalkene and a reducing substrate in the presence of a peroxidase in a solvent for the reaction to produce 1-hydorxy-n-phenyl-(n-1)-alkene as a hydroxyalkene wherein the alkene group contains 3 to 8 carbon atoms and n is 5, 6, 7 or 8 and wherein phenyl is substituted or unsubstituted;
   (b) separating the hydroperoxyalkene and hydroxyalkene from the reacted mixture;
   (c) determining the concentration of the hydroperoxyalkene or hydroxyalkene based upon a liquid chromatographic separation; and
   (d) determining the activity of the peroxidase or the reducing substrate based upon the concentration of the hydroperoxyalkene or hydroxyalkene in the chromatographic separation in the assay.

2. The method of claim 1 wherein the peroxidase is horseradish peroxidase and the reducing substrate is a compound to be tested for reducing substrate capability.

3. The method of claim 1 wherein the peroxidase is unknown and wherein the reducing substrate has a capability to act as the reducing substrate in the presence of a standard peroxidase which is assayed and then compared in a separate assay to the capability of the unknown peroxidase in the presence of the reducing substrate.

4. The method of claim 3 wherein the standard peroxidase is horseradish peroxidase.

5. A method for assay of peroxidase or the ability of compound to serve as a reducing substrate in a peroxidase catalized reaction which comprises:
   (a) reacting a mixture of 1-hydroperoxy-5-phenyl-4-pentene as a hydroperoxypentene and a reducing substrate in the presence of a peroxidase in a solvent for the reaction to produce 1-hydroxy-5-phenyl-4-pentene as a hydroxypentene;

(b) separating the hydroperoxypentene and hydroxpentene from the reacted mixture;

(c) determining the concentration of the hydroperoxy pentene or hydroxypentene based upon a liquid chromatographic separation; and (d) determining the activity of the peroxidase or the reducing substrate based upon the concentration of the hydroperoxypentene or hydroxypentene in the chromatographic separation in the assay.

6. The method of claim 5 wherein the peroxidase is horseradish peroxidase and the reducing substrate is a compound to be tested for reducing substrate capability.

7. The method of claim 5 wherein the peroxidase is unknown and wherein the reducing substrate has a capability to act as the reducing substrate in the presence of a standard peroxidase which is assayed and then compared in a separate assay to the capability of the unknown peroxidase in the presence of the reducing substrate.

8. The method of claim 7 wherein the standard peroxidase is horseradish peroxidase.

9. The method of claim 5 wherein the reactant hydroperoxypentene and the hydroxypentene are separated from the mixture by solid phase extraction.

10. The method of claim 9 wherein the solid phase extraction is conducted on octadecyl silica gel columns.

11. The method of claim 5 wherein the chromatographic separation is by high performance liquid chromatography.

12. The method of claim 5 wherein a standard compound which separates at a particular place is provided in the chromatographic separation as a reference.

13. The method of claim 12 wherein the internal standard is p-nitrobenzyl alcohol.

14. The method of claim 11 wherein ultraviolet light is used to determine compounds in the chromatographic separation.

15. A kit for assay of peroxidase or the ability of a compound to serve as a reducing substrate in a peroxidase catalized reaction which comprises:

(a) 1-hydroperoxy-n-(n-1)-alkene as a hydroperoxyalkene;

(b) a peroxidase; and (c) a chromatographic column for separating the hydroperoxyalkene or a 1-hydroxy-n- phenyl-(n-1)alkene as a hydroxyalkene produced therefrom by the peroxidase enzyme wherein phenyl is substituted or unsubstituted and wherein (a), (b) and (c) are provided in separate containers.

16. The kit of claim 15 wherein the peroxidase is prostaglandin H synthase.

17. The kit of claim 15 wherein peroxidase is horseradish peroxidase.

18. In a method for determining peroxidase activity or a reducing substrate activity for the peroxidase the improvement which comprises:

(a) reacting an effective amount of a mixture of 1-hydroperoxy-n-phenyl-(n-1)-alkene as a hydroperoxyalkene and a reducing substrate in the presence of the peroxidase in a solvent for the reaction to produce 1-hydroxy-n-phenyl-(n-1)-alkene as a hydroxyalkene wherein the alkene group contains 3 to 8 carbon atoms and n is 5, 6, 7 or 8 and wherein phenyl is substituted or unsubstituted; and (b) determining the activity of the peroxidase or the reducing substrate based upon the concentration of the hydroperoxyalkene or the hydroxyalkene produced by the reaction.

* * * * *

UNITED STATES PATENT AND TRADEMARK OFFICE
CERTIFICATE OF CORRECTION

PATENT NO.  : 4,780,281
DATED       : 1988 October 25
INVENTOR(S) : Lawrence J. Marnett and Paul E. Weller It is certified that error appears in the above—identified patent and that said Letters Patent is hereby corrected as shown below:

In the Abstract, line 10, "in" should be --is--.

Column 1, line 65 "Puffler" should be --Putter--.

Column 2, line 32 "HPLC)" should be -- (HPLC) --.

Column 6, line 18 "reminder" should be --remainder--.

Column 8, line 63 "ubstrates" should be --substrates--.

Column 9, line 44 "spectrophtometric" should be --spectrophotometric--. .

Column 9, line 48 "quaiacol" should be --guaiacol--.

Column 10, line 17, in Table 1, "12", first occurrence, should be --11--.

UNITED STATES PATENT AND TRADEMARK OFFICE
CERTIFICATE OF CORRECTION

PATENT NO. : 4,780,281

DATED : 1988 October 25

INVENTOR(S) : Lawrence J. Marnett and Paul E. Weller

It is certified that error appears in the above—identified patent and that said Letters Patent is hereby corrected as shown below:

Column 10, line 45 "protaglandin" should be --prostaglandin--.

Column 10, line 63 "apprximately" should be --approximately--.

Column 11, line 57 "benzo[a]yrene" should be --benzo[a]pyrene--.

Column 12, line 37 "1-hydorxy" should be --1-hydroxy--.

Column 13, line 3, "hydrox-" should be --hydroxy--.

Signed and Sealed this

Twenty-third Day of May, 1989

Attest:

DONALD J. QUIGG

Attesting Officer

Commissioner of Patents and Trademarks